United States Patent [19]

Wang et al.

[11] Patent Number: 5,714,110

[45] Date of Patent: Feb. 3, 1998

[54] PROCESS IMPROVEMENTS FOR PREPARING CATHETER BALLOONS

[75] Inventors: Lixiao Wang, Maple Grove; Paul James Miller, St. Louis Park; Daniel J. Horn, Shoreview; Deborah A. Frank, St. Louis Park, all of Minn.

[73] Assignee: SciMed Life Systems, Inc., Maple Grove, Minn.

[21] Appl. No.: 650,222

[22] Filed: May 20, 1996

Related U.S. Application Data

[63] Continuation of Ser. No. 197,634, Feb. 17, 1994, abandoned, which is a continuation-in-part of Ser. No. 124,238, Sep. 20, 1993, abandoned.

[51] Int. Cl.$^6$ ............................ B29C 49/08; B29C 49/18
[52] U.S. Cl. ................... 264/529; 264/532; 264/573; 604/96; 606/194
[58] Field of Search .................... 606/194, 192; 604/96; 264/529, 530, 532, 570, 573

[56] References Cited

U.S. PATENT DOCUMENTS

| | | | |
|---|---|---|---|
| Re. 32,983 | 7/1989 | Levy | 428/36.92 |
| Re. 33,561 | 3/1991 | Levy | 428/36.92 |
| 4,002,709 | 1/1977 | Mozer | 264/535 |
| 4,006,729 | 2/1977 | Van Cappellen | 126/518 |
| 4,156,466 | 5/1979 | Leslie et al. | 172/4.5 |
| 4,249,971 | 2/1981 | Yap et al. | 156/143 |
| 4,254,774 | 3/1981 | Boretos | 604/271 |
| 4,413,989 | 11/1983 | Schjeldahl et al. | 604/96 |
| 4,443,399 | 4/1984 | Takashiege et al. | 264/519 |
| 4,456,000 | 6/1984 | Schjeldal et al. | 604/53 |
| 4,490,421 | 12/1984 | Levy | 428/36.9 |
| 4,550,007 | 10/1985 | Ohtsu et al. | 264/521 |
| 4,906,244 | 3/1990 | Pinchuk et al. | 606/194 |
| 4,938,676 | 7/1990 | Jackowski et al. | 425/140 |
| 4,952,357 | 8/1990 | Euteneuer | 264/129 |
| 4,963,313 | 10/1990 | Noddin et al. | 264/573 |
| 5,011,648 | 4/1991 | Garver et al. | 264/532 |
| 5,087,394 | 2/1992 | Keith | 264/22 |
| 5,108,415 | 4/1992 | Pinchuk et al. | 606/194 |
| 5,156,612 | 10/1992 | Pinchuk et al. | 606/194 |
| 5,264,260 | 11/1993 | Saab | 428/35.5 |

(List continued on next page.)

FOREIGN PATENT DOCUMENTS

| | | |
|---|---|---|
| 274 411 | 7/1988 | European Pat. Off. . |
| 485 903 | 5/1992 | European Pat. Off. . |
| 540 858 | 5/1993 | European Pat. Off. . |
| 420 488 | 7/1993 | European Pat. Off. . |
| 0-318-919-B1 | 1/1994 | European Pat. Off. . |
| 89/08473 | 9/1989 | WIPO . |
| 92/08512 | 5/1992 | WIPO . |
| 92/19316 | 12/1992 | WIPO . |
| 92/19440 | 12/1992 | WIPO . |

OTHER PUBLICATIONS

S. A. Jabarin and E. A. Lofgren, "Effects of Water Absorption on Physical Properties and Degree of Molecular Orientation of –Poly(Ethylene Terephthalate)," – Unknown date, unknown publication.

Levy, "Improved Dilation catheter Balloons." *J. Clinical Engineering*, 11, pp. 291–296 (1986), Jul. 1986.

*Primary Examiner*—Catherine Timm
*Attorney, Agent, or Firm*—Vidas, Arrett & Steinkraus

[57] ABSTRACT

A method for forming a balloon for a dilatation catheter may utilize the steps of extruding a tubing preform of a polyester resin and then blowing the tubing into an oriented balloon, wherein the tubing preform is dried prior to blowing into the balloon form. Other process steps by which balloon cone and waist thicknesses may be reduced involve varying the axial tension and blowing pressure at several stages as a mold containing the balloon preform is dipped into a heating medium. Specifically, tubing of a thermoplastic material is placed in a mold and blown by pressurizing and tensioning the tubing and gradually dipping the mold into a heated heat transfer media so as to sequentially blow a first waist, a body and a second waist portion. The tubing is subjected to a relatively lower pressure while the body portion is blown than while the first and second waist portions are blown.

16 Claims, 4 Drawing Sheets

U.S. PATENT DOCUMENTS

| | | | |
|---|---|---|---|
| 5,290,306 | 3/1994 | Trotta et al. | 606/194 |
| 5,304,340 | 4/1994 | Downey | 264/521 |
| 5,395,333 | 3/1995 | Brill | 606/194 |
| 5,403,340 | 4/1995 | Wang et al. | 606/194 |
| 5,411,477 | 5/1995 | Saab | 606/194 |
| 5,496,276 | 3/1996 | Wang et al. | 606/194 |

PROCESS IMPROVEMENTS FOR PREPARING CATHETER BALLOONS

CROSS-REFERENCE TO RELATED APPLICATIONS

This application is a continuation of U.S. patent application Ser. No. 08/197,634, filed Feb. 17, 1994, now abandoned, which is a continuation-in-part of U.S. patent application Ser. No. 08/124,238, filed Sep. 20, 1993, now abandoned.

BACKGROUND OF THE INVENTION

The present invention relates to a method for making balloons for catheters used in medical dilatation procedures.

Balloon catheters are being used extensively in procedures related to the treatment of blood vessels. For example, arterial stenosis is commonly treated by angioplasty procedures which involve inserting balloon catheters into specific arteries. Balloon catheters have also been found useful in procedures involving dilation of body cavities.

The most widely used form of angioplasty makes use of a dilatation catheter which has an inflatable balloon at its distal end. Using fluoroscopy, a physician guides the catheter through the vascular system until the balloon is positioned across the stenoses. The balloon is then inflated by supplying liquid under pressure through an inflation tureen to the balloon. The inflation of the balloon causes stretching of a blood vessel and pressing of the lesion into the blood vessel wall to reestablish acceptable blood flow through the blood vessel.

In order to treat very tight stenoses with small openings, there has been a continuing effort to reduce the profile of the catheter so that the catheter can reach and pass through the small opening of the stenoses. There has also been an effort to reduce the profile of the catheter after an initial use and deflation of the balloon to permit passage of the catheter through additional lesions that are to be treated or to allow entry and retreatment of lesions that reclose after initial treatment.

One factor manipulated to reduce the profile of the dilatation catheter is the wall thickness of the balloon material. Balloons for dilatation balloon catheters have been made from a wide variety of polymeric materials. Typically the balloon wall thicknesses have been on the order of 0.0004 to 0.003 inches for most materials. There have been continuing efforts, however, to develop ever thinner walled balloon materials, while still retaining the necessary distensibility and burst pressure rating, so as to permit lower deflated profiles.

It is possible to make balloons from a variety of materials that are generally of the thermoplastic polymeric type. Such materials may include: polyethylenes and ionomers, ethylene-butylene-styrene block copolymers blended with low molecular weight polystyrene and, optionally, polypropylene, and similar compositions substituting butadiene or isoprene in place of the ethylene and butylene; poly(vinyl chloride); polyurethanes; copolyesters; thermoplastic rubbers; silicone-polycarbonate copolymers; polyamides; and ethylene-vinyl acetate copolymers. Orientable polyesters, especially polyethylene terephthalate (PET), are among the preferred materials for forming catheter balloons.

References illustrating the materials and methods of making catheter balloons include: U.S. Pat. No. 4,413,989 and U.S. Pat. No. 4,456,000 to Schjeldahl et al, U.S. Pat. Nos. Re 32,993 and Re 33,561 to Levy, and U.S. Pat. No. 4,906,244, U.S. Pat. No. 5,108,412 and U.S. Pat. No. 5,156,612 to Pinchuck et al. The Levy patents, teach that a high tensile strength polyethylene terephthalate balloon can only be formed from a high intrinsic viscosity polymer, specifically, high molecular weight polyethylene terephthalate having a requisite intrinsic viscosity of at least 1.0.

High tensile strengths are important in angioplasty balloons because they allow for the use of high pressure in a balloon having a relatively small wall thickness. High pressure is often needed to treat some forms of stenosis. Small wall thicknesses enable the deflated balloon to remain narrow, making it easier to advance the balloon through the arterial system.

Polyesters possessing a lower intrinsic viscosity are easier to process, and hence balloon manufacturers have desired to use polyesters possessing an intrinsic viscosity below 1.0. However, it was thought that using such material would sacrifice the strength of the balloon. Recently it has been discovered that angioplasty catheter balloons, having a wall strength of greater than 30,000 psi and a burst strength of greater than 300 psi, can be prepared from a PET polymer of an intrinsic viscosity of 0.64–0.8. This, high strength, non-compliant balloon, made from a standard intrinsic viscosity polyester, has been a significant improvement in the art. There remains, however, a need to continue to improve balloon wall strengths while simultaneously reducing their wall thickness.

Prior art PET balloon forming techniques involve blowing or stretching and blowing of the balloon in a segment of extruded PET tubing. It has been recognized that control of moisture in the PET resin, prior to extrusion, is important and prior art techniques have embodied a drying step prior to extrusion of PET tubing from which the balloon is formed by stretch blow molding techniques. However it has not been previously suggested that drying of extruded tubing would provide any benefit properties of the balloons produced from the extruded tubing.

Balloons produced by stretching and blowing a tubular preform or "parison" typically have much thicker waist and cone walls than the wall thickness of their body portions. The thicker cone walls contribute to the overall thickness of the catheter, making tracking, crossing and recrossing of lesions more difficult. Further, thick cones interfere with refolding of the balloon on deflation so that the deflated balloon can only be further inserted or withdrawn with difficulty, occasionally even damaging the blood vessel.

There have been several solutions proposed for reducing the cone or waist thickness of catheter balloons in U.S. Pat. No. 4,906,241, U.S. Pat. No. 4,963,313, and EP 485,903. However, the procedures involved in these references are quite cumbersome and so it is desirable that simplified methods be developed to provide cone and waist walls with reduced thicknesses.

SUMMARY OF THE INVENTION

The present invention in one aspect is an improved method for forming a balloon for a dilatation catheter involving the steps of extruding a tubing preform of a polyester resin and then blowing the tubing into an oriented balloon, the improvement comprising that the tubing preform is dried prior to blowing into the balloon form. The addition of this novel step to the balloon forming method has been observed to cause a reduction in the frequency of balloons which are rejected because of defects in the balloon wall while producing the same or higher wall strengths in the non-defective balloons obtained.

It has also been discovered that the problem of thick balloon cones and waists can be substantially improved by varying the axial tension and blowing pressure at several stages as a mold containing the balloon preform is dipped into a heating medium. A further aspect of the invention therefore is an improved method of forming a balloon for a catheter, comprising placing tubing of a thermoplastic material in a mold and blowing the balloon by pressurizing and tensioning the tubing and gradually dipping the mold into a heated heat transfer media so as to sequentially blow the first waist, the body and the second waist portions of the balloon, the tubing being subjected to a relatively lower pressure, and preferably a relatively a lower tension, while the body portion is blown than while the first and second waist portions are blown.

DETAILED DESCRIPTION OF THE PREFERRED EMBODIMENTS

Figure 1:
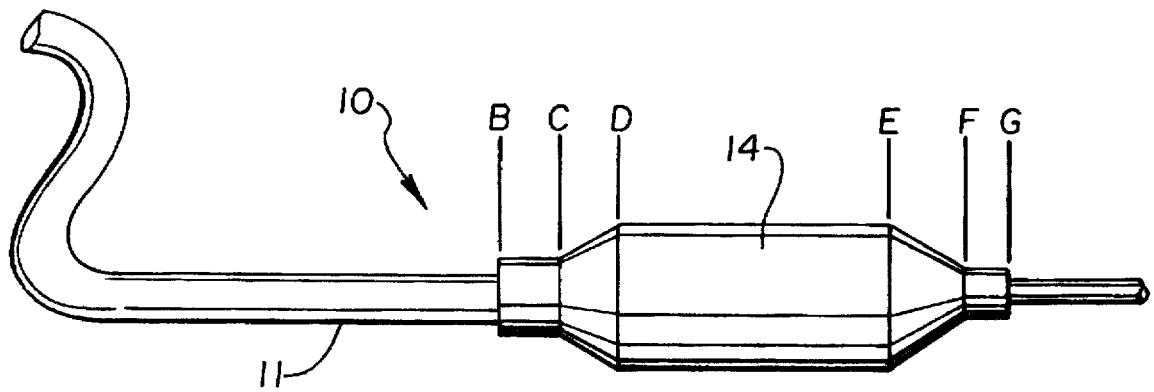
FIG. 1 is a perspective view of an angioplasty catheter having a balloon of the invention mounted thereon.

A dilatation balloon catheter of the present invention, illustrated generally at 10 in FIG. 1, includes an inflatable balloon 14 mounted at the distal end of an elongated flexible shaft 11. Catheter 10 is conventional in its construction, providing a lumen communicating with the interior of balloon 14, for inflation and deflation of the balloon, and other optional features conventional in the dilatation catheter art. The balloon 14 is in its inflated configuration. The balloon 14 is formed of a thermoplastic polymer material which provides the balloon with its essential compliance characteristics. The balloon may be noncompliant and made of stiff materials such as PET or nylon, or it may be compliant, made of polyester copolymers, blends of polyesters or blends of a polyester with a minor portion of another thermoplastic polymer which disrupts the crystallinity of the polyester. Other thermoplastic materials such as previously described for catheter balloons may be employed. Most advantageously the balloon material is a polyester; a polyamide or similar highly orientable polymer material.

The balloon of this invention, in one aspect, is obtained by extruding tubing of a thermoplastic polymer comprising a polyester, drying the tubing, suitably for at least 4 hours, and preferably at least 24 hours, and then expanding the extruded tubing axially and radially. In this drying step the tubing is suitably dried to a moisture content weight of 0.15% or less, by any suitable means, including vacuum drying with or without heat and with or without a desiccant.

Figure 2A:
FIGS. 2a, 2b and 2c illustrate the results of various process steps in forming a catheter balloon, depicting respectively, side elevational views of an extruded tube of polymer material used to form the balloon, a stretched tubing preform prepared from the extruded tube, and a formed balloon prepared from the stretched tubing preform.
Figure 2B:
Figure 2C:
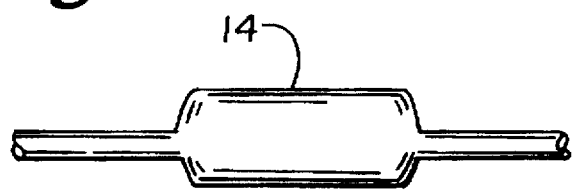

Any conventional extruder may be employed to perform the extrusion process. After the resin has been extruded into tube form and dried, it preferably undergoes a prestretch which axially elongates the tubing. Referring to FIGS. 2a–2c, the prestretching process comprises applying an axial stretching force to the extruded tubing 12, heating the extruded tubing, allowing the extruded tubing to stretch while maintaining the axial stretching force and finally cooling the stretched tubing 13. Once the prestretch is complete, the stretched tubing 13 is radially expanded into the form of a balloon 14, using a molding process. The molding process comprises placing the stretched tubing 13 in a mold, heating the mold and expanding the stretched tubing radially by means of internal pressure. After sufficient time has passed for the balloon to form, the mold is cooled and the balloon 14 is removed.

The starting resin used to produce the balloon of this invention is most preferably a PET homopolymer or copolymer. The resin should be relatively free of foreign material and other contaminants. Polyethylene terephthalate in pellet form may be employed. Suitable examples are Shell Chemical's "Cleartuf 7207" and "Traytuf 7357", and DuPont's "Selar X260". The intrinsic viscosity of the PET resin is preferably between 0.64–0.80, more preferably between 0.68–0.76 and most preferably between 0.72–0.74. Intrinsic viscosity, which is a function of the molecular weight, may be determined by means of manufacturer standard processes, or ANSI/ASTM D 2857-70.

Well controlled processing of the PET resin is important to attaining the desired strength and compliance characteristics in the final balloon. The PET resin is preferably dried to less than 10 ppm moisture content prior to extrusion. Drying to this level prevents excessive degradation of the material during extrusion and also reduces other defects such as tubing haziness or bubbles.

Once the pellets have been sufficiently dried, they are extruded under carefully controlled conditions. As stated previously, any conventional extruder may be employed to perform the extrusion. Suitably, a Killion extruder with a 1.25 inch diameter barrier flight screw is used.

In order to obtain optimal results, the processing temperatures applied to transform the raw resin into balloon preform tubing are meticulously maintained. A preheater may be employed that permits the use of a small extruder while still maintaining normal torque levels. The preheater heats the resin to 370° F. Thereafter, the pellets move to the feedthroat which is maintained at a temperature of 140°–180° F. Next, the PET material passes through three extruder zones, the first of which is preferably maintained at 490° F. (+/−5° F.) while the following two are maintained at 500° F. (+/−5° F.). The PET material then passes through a clamp and a melt filter before it reaches the die. The clamp, melt filter and two temperature zones within the die are all maintained at 500° F. (+/−5° F.). The melt filter removes foreign matter from the PET material, thereby ensuring a correct failure mode in the final balloons. Optimally, the residence time in the extruder is kept to a minimum. The preferred die size is in the range of 0.060–0.080 inches.

After the PET material extrudes out of the die in tube form, it must be cooled. One way to perform the cooling process is to pass the extruded tubing from the extruder, through a small air gap and into a water bath maintained at approximately 60°–70° F. A puller may be used to pull the tube from the cooled end through the water bath. Thereafter, the tubing is cut into lengths. The area draw down ratio of the extruded tubing (which is the area defined by the die and mandrel divided by the cross-sectional area of the extruded tubing) should be less than 10.

After the tubing has been extruded and cut, it is preferably prestretched to axially elongate the tubing prior to its radial expansion. In the past it was considered important to prestretch and mold the balloon soon after the tube had been extruded, to reduce the chance that the tube would not be degraded by atmospheric moisture. Immediate prestretching and blowing is sometimes inefficient in a commercial manufacturing operation, however, and was not a fully reliable method of assuring a uniform yield of high quality balloons. It has now been discovered that the negative effects of exposure to atmospheric moisture can readily be avoided or reversed by desiccating the extruded tubing, preferably to a moisture content of no more than 0.15 weight %. In accordance with one aspect of the invention, therefore, the preform is dried between the extrusion and blowing steps, suitably between extrusion and prestretching. Drying may be accomplished by heating the extruded tubing at 50° C.–60° C. in a vacuum oven, suitably at a pressure of $10^{-6}$ atm or less; or in a desiccator containing a conventional desiccant suitably at a pressure of 600–760 mm Hg, at ambient temperature. The tubing is dried for a period of at least 4 hours, preferably 24 hours, more preferably at least 48 hours, or until a sample preform of a batch introduced simultaneously into the desiccator is measured to have a moisture content of no more than 0.15%, preferably less than 0.10%, more preferably less than 0.075%, water. Examples of suitable desiccants which may be employed to aid in drying the tubing include silica gel, molecular sieves, for instance molecular sieves 3A and 4A, calcium chloride, phosphorus pentoxide, and Drierite™. A combination of heat, vacuum and desiccant may be used to obtain the necessary dryness in a shorter period of time if desired.

The prestretch step stretches a section of a cut length of tubing to a predetermined length by applying an axial stretching force to the tube while the tube is heated. Once the tube is exposed to the higher temperature, the axial stretching force is maintained and the tubing is stretched at a specific rate. Desirably, the tube is heated just prior to stretching.

Figure 3:
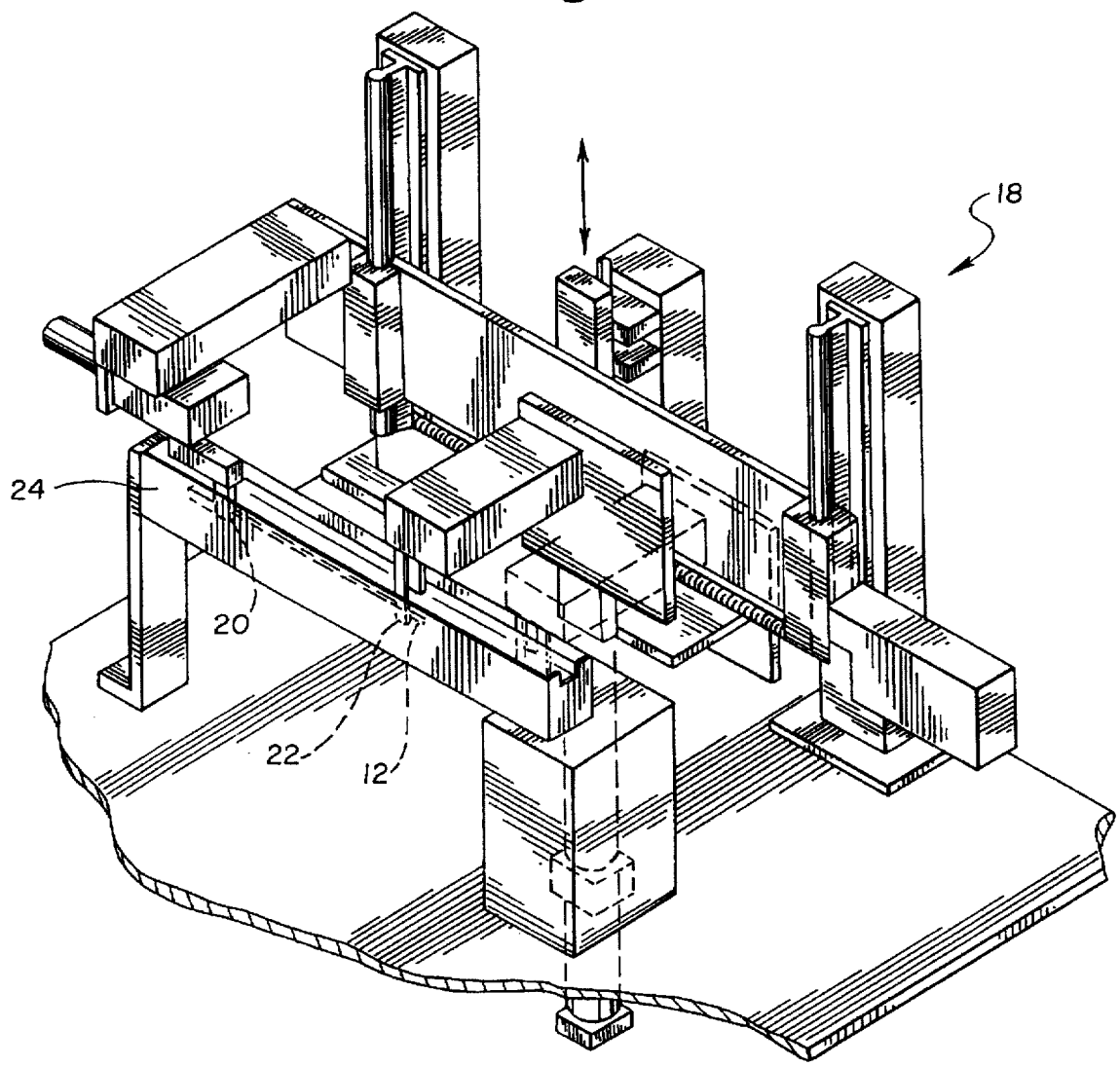
FIG. 3 is a schematic view of a stretching device that may be useful in practicing the method of the invention.

FIG. 3 illustrates one device useful in performing the prestretch. The device 18 of FIG. 3 possesses two jaws 20 and 22 capable of gripping at least one cut length of extruded tubing 12. The stretching device 18 lowers the tubing 12 into a bath 24 containing heated media maintained at a temperature above the glass transition temperature of the extruded tubing 12. A suitable temperature is the range extending from 85°–95° C. However, the preferred media is water at a temperature of 90° C. (+/–2° C.). The first gripping jaw 20 may remain stationary while the second gripping jaw 22 moves horizontally at a set rate to a predetermined final position, thereby achieving the desired final stretch. The preferred rate of stretching is 25% per second. The desired mount of axial elongation prior to radial expansion is in the range of 75–150%. Preferably, however, the axial elongation occurring in this phase is 125%. Therefore, the stretch ratio, calculated by dividing the final length of the stretched section of tubing (the portion between jaws 20 and 22) by the initial length of that section, is 2.25.

After the tubing 12 is stretched to the desired stretch ratio and length, it is cooled. This may be accomplished with a device such as the device 18 of FIG. 3 by controlling the jaws 20 and 22 such that they finish stretching the tubing 12 and automatically lift up out of the bath 24. The stretched tubing 13 may then be moved to a cooling water bath (not shown), preferably maintained at room temperature. During this cooling process, the stretched tubing portion 13 of tubing 12 is held on both ends in order to apply sufficient tension to ensure that the tube does not relax and shrink or recover from the stretch.

Figure 4:
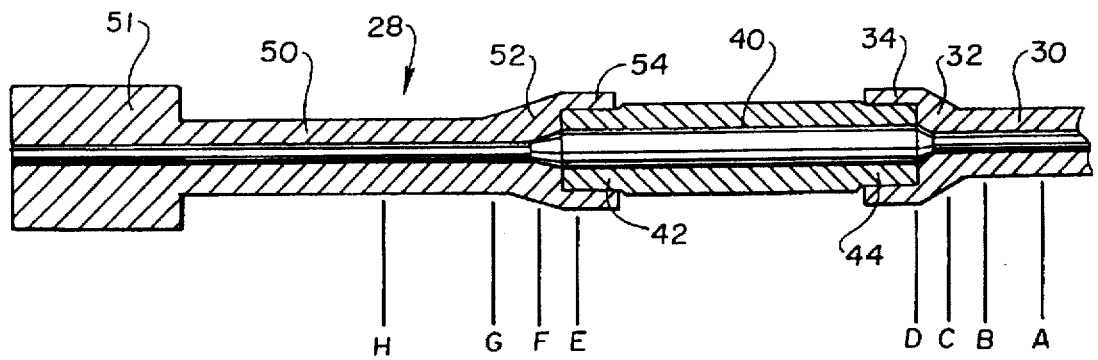
FIG. 4 is a cross-sectional view of a preferred mold used in the method of the invention.

After cooling, the stretched tubing 13 is removed from the water bath and expanded radially using internal pressure. The dimensions to which it is stretched are preferably controlled by performing the radial stretching while the tubing 13 is in a mold having the shape of the desired balloon. A suitable mold 28 is shown in FIG. 4. Heating the stretched tubing 13 while radially expanding it may best be accomplished by dipping the mold 28 into hot water while internal pressure is applied.

To perform the radial expansion step one end of the stretched tube inside of the area where it was gripped by jaws 20 and 22 is cut off to provide an opening to the lumen of the tubing 13. The stretched tube 13 then fed through the mold 28 which consists of three parts: the proximal portion (top) 30, the body 40 and the distal (bottom) portion 50. These three sections fit tightly together and provide the tubing 13 a form to blow to.

Figure 5:
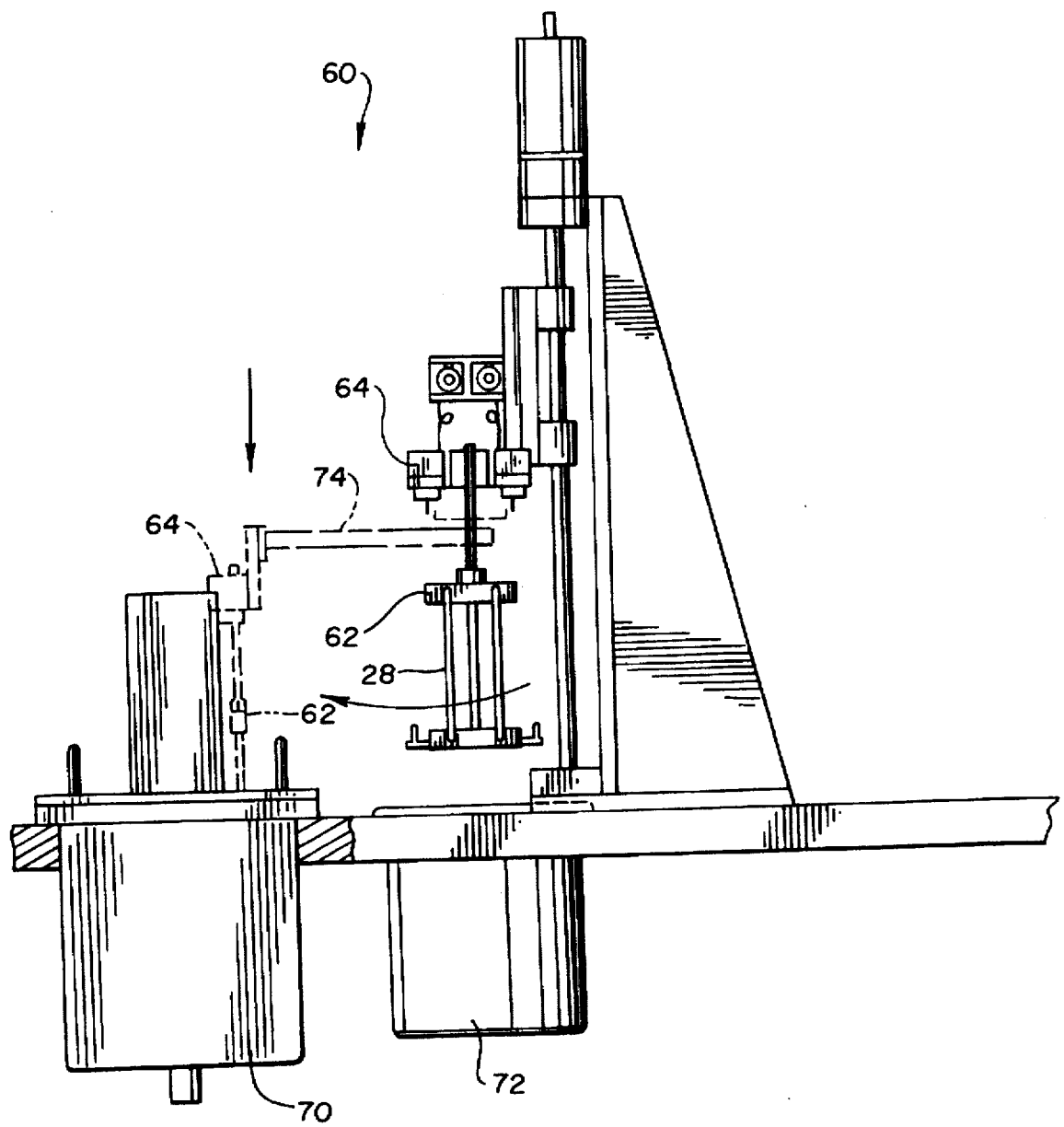
FIG. 5 is a side elevation view of a molding station that may be useful in practicing the method of the invention.

Referring to FIG. 4, the distal portion 50 of the preferred mold 28 is generally between 0.6 and 1.4 inches long, which includes the enlarged end section 51 used to hold the mold 28 in the molding fixture 62 (FIG. 5). The distal cone section 52 is formed at an angle of between 15° and 45° with the axis of the mold 28. The cup 54 of the distal portion, which interfaces with the distal insert portion 42 of body 40, generally has a length of 0.120 inches. The proximal portion 30 of the preferred mold 28 is generally between 1.1 and 2.0 inches long. The proximal cone section 32 is also formed at an angle of between 15° and 45° with the axis of the mold 28. The cup 34 of the proximal portion interfaces with the proximal insert portion 44, symmetrical with the distal insert mold portion 42 of body 40. The length for the balloon body 40 is generally between 0.4 and 2 inches long. The inner and outer diameter of the mold sections 30, 40 and 50, and the angles of each cone 32, 52 are both dependent on the desired balloon size. The mold 28 for the balloon will be different when producing different sized balloons, which is necessary to meet the preference or needs of those who will perform medical treatments with the balloon.

The molds 28 of the present invention are preferably made of 303 stainless steel with a smooth mirror finish to provide a smooth finish on the balloon surface. The surface roughness average should be in the range of 5–10 microns or less.

Figure 6:
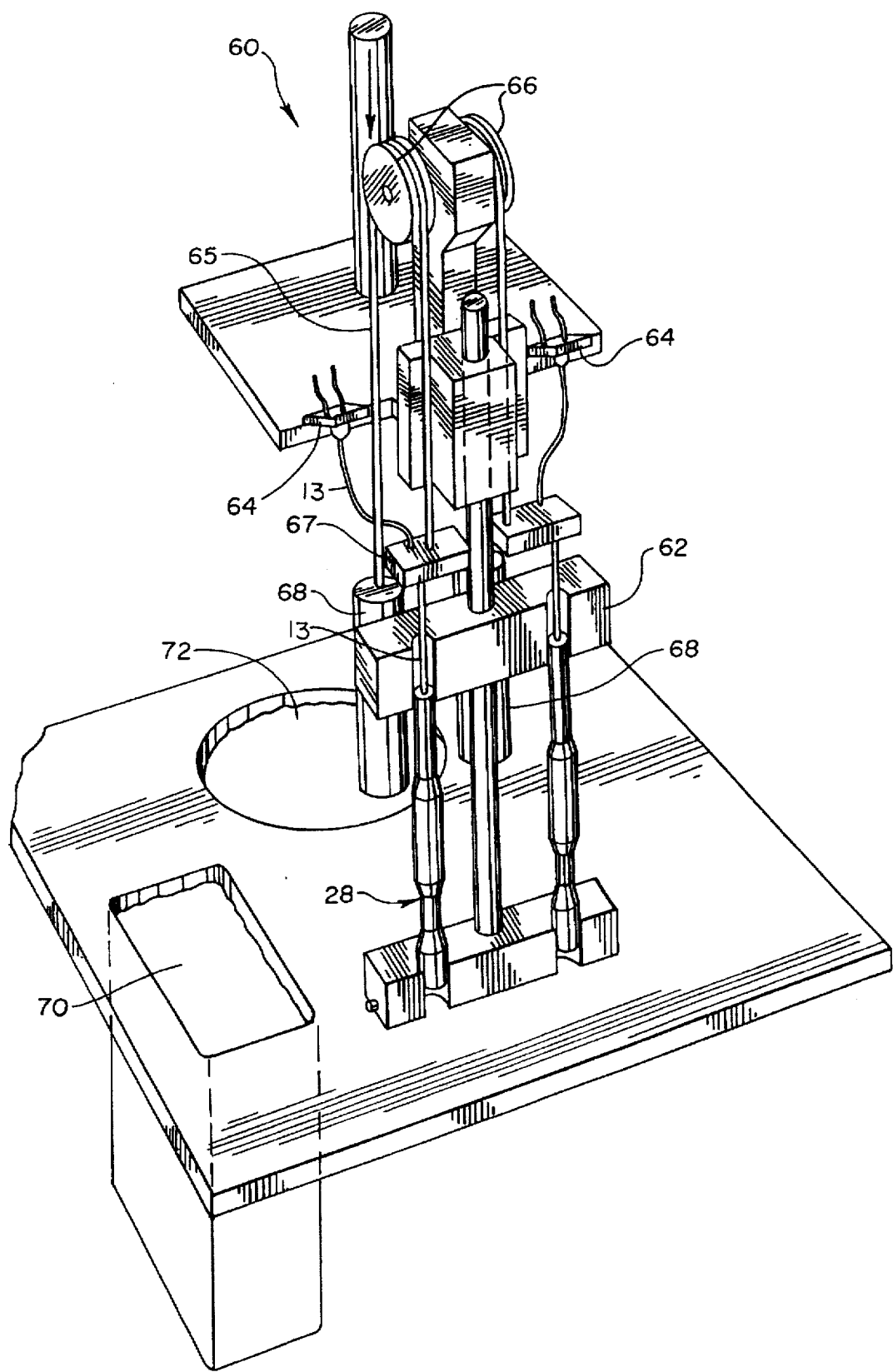
FIG. 6 is a perspective schematic representation of relevant portions of the molding station of FIG. 5.

The appropriate mold 28, with the stretched tubing 13 inside, may be heated while pressure is applied using a device 60 such as the one depicted in FIGS. 5 and 6. With this device 60, the mold 28 is placed in a holder 62. The tubing 13 extends out from the top of the mold 28 and is fed into a Touhy clamp 64 through which a pressurized fluid, preferably nitrogen gas, is applied to the inner lumen of the tubing 13. The tubing at the bottom of the mold 28 is clamped off such that no gas can flow through it. The pressure applied is suitably in the range of 210–280 psi.

One advantage of using a device 60 is that tension may be applied to the tubing 13 during the molding phase. A string 65 trained over pulley 66 (shown in FIG. 6 but deleted from FIG. 5 for sake of clarity) may be attached to a tension clamp 67 adjacent the Touhy clamp 64. The tension clamp 67 holds the tubing 13 to apply tension to it without closing off the flow path of pressurized fluid into tubing 13. Weights 68 attached to the end of string 65 may thus provide tension to the tubing 13. Generally, 0–500 g of tension may be applied. Tension may be applied during the molding process to better control the wall thickness of certain areas of the balloon, primarily the waist sections. I The tension decreases the cross sectional area of the balloon waists, thereby increasing flexibility in those regions.

The tubing 13, subjected to specific interior pressures, is then heated. As depicted by dashed lines in FIG. 5, the mold 28 is dipped into a water bath 70, suitably at a rate of 4 mm/sec., with the total process of submerging the mold 2.3 inches into the bath 70 taking approximately 15 seconds. Preferably, the bath 70 is a hot water bath maintained at a temperature range of 85°–98° C., with 95° C. (+/–1° C.) being the most preferred temperature. Once the entire mold 28 has been submerged it is held stationery for a period of time, suitably 40 seconds, while the balloon and waist portions yield completely and stabilize. The radial expansion, or hoop ratio (calculated by dividing the inner diameter of the balloon by the inner diameter of the extruded tubing), should be in the range of 6–8.5. However, the preferred hoop ratio is approximately 8.0. A lower hoop ratio may result in compliance which is higher than desired. A higher hoop ratio may result in preforms which will not blow out fully. During this phase of radial expansion, the tubing 13 will further elongate, i.e. expand further in the axial direction, such that the total elongation of the tubing 13 in the finished balloon body will range from 175–275% of the length of the unstretched tubing used to form the body of the balloon.

In accordance with a further aspect of the invention the stretched tubing 13 is blown during a programmed dipping cycle, for dipping into hot water bath 70, during which the pressure and axial tension are varied at several stages so that the balloon is sequentially blown from one end to the other (proximal, body and distal, or vice versa). By this method, a reduced waist and cone thickness is obtained without the necessity of introducing a separate processing operation directed specifically to cone and waist reduction.

FIG. 4 has been labeled to show depth regions at which transitions of pressure and/or tension occur in this aspect of the invention as mold 28 is dipped into bath 70. Corresponding locations on the balloon 14 are labeled in FIG. 1. The region B-C comprises the proximal waist portion, the region C-D comprises the proximal cone portion, the region D-E comprises the body portion, the region E-F comprises the distal cone portion and the region F-G comprises the distal waist portion of the mold. The balloon blowing process of the invention involves the steps of:

pressurizing the stretched tubing to a first pressure in the range of 150–320 psi and applying a first tension in the range of 5–150 g;

dipping the mold to a first depth in the range of from the transition (C) from the first waist to the first cone to the transition (D) from the first cone to the body portion of the balloon;

reducing the pressure to a second pressure between 80 and 170 psi and setting a second tension in the range of the first tension;

dipping the mold to a second depth in the range of from the transition (E) from the body portion to the second cone portion to the transition (F) from the second cone to the second waist;

increasing the pressure to a third pressure higher than the second pressure and between 150 and 320 psi and increasing the tension to a third tension, higher than the first and second tensions, and then, dipping the mold to a third depth (H) beyond the depth (G) of the second waist.

Although the process may be accomplished with substantially continuous dipping, it is preferred that the mold be held at each of the first, second and third depths for predetermined time intervals before changing pressure/tension parameters and moving to the next depth. Suitable hold time intervals are between 1 and 40 seconds at the first depth, between 1 and 40 seconds at the second depth and between 10 and 100 seconds at the third depth. A typical dipping program for a PET polymer balloon, beginning at an initial depth (A) before the depth (B) of the first waist of the balloon, and using a 95° C. hot water bath as heating media, will take a total of approximately 60–90 seconds. Typical programs for PET balloons are illustrated in Examples 4–9.

The third tension is suitably in the range of 50 to 700 g, and is higher than the second tension, suitably higher than both the first and second tensions. For balloons of 4.00 mm diameter or less, the third tension will usually not exceed 500 g. The second tension may be the same or different from the first tension and if different will usually be less than the first tension. In general the tension employed at all depths will be higher as the diameter of the balloon is increased. For balloons having nominal diameters of at least 2.25 mm it is preferred that the third tension be higher than both the first and second tensions by at least 150 grams and at all typical angioplasty balloon diameters it is preferred that the difference between the second and third pressures be at least 100 psi, usually at least 150 psi.

It should be noted that this aspect of the invention can also be practiced by inserting the end of mold 28 which forms the distal end of the balloon into the heating bath first.

The balloon formed in the mold is next cooled. One way to cool the balloon is to remove the mold 28 from the hot water bath 70 and place it in a cooling bath 72. As shown in FIG. 5, this step may be accomplished through use of a machine 60 having a pivot arm 74 capable of transferring the mold 28 from the hot 70 to the cold water bath 72. The cooling bath 72 is preferably maintained at 7°–15° C. In the preferred embodiment, the balloon remains in the cooling bath 72 for approximately 10 seconds.

Finally, the ends of the tubing 13 extending from the mold 28 are cut off and the balloon is removed from the mold 28 by removing either the distal end 50 or proximal end 30 from the body section 40 of mold 28, then gently pulling the balloon from the remaining mold sections. To mount on a catheter 10, balloon 14 is cut at B and G and adhered to the catheter in conventional manner.

The various aspects of the invention are illustrated by the following non-limiting examples. In the examples wall thickness measurements are single wall thicknesses unless specifically specified as double wall thicknesses.

EXAMPLE 1

Post Extrusion Drying

The product of this example is a 3.00 mm balloon. Shell Chemical Cleartuf 7207 PET pellets, reported as having an intrinsic viscosity of 0.73 as determined by Goodyear R100E intrinsic viscosity test method, were dried to approximately 10 ppm moisture content. The dried resin was extruded into tubing and cut into 8 inch sections. The tubing sections had an OD of 0.0425 in. and an ID of 0.0183 in.

The extruded tubing sections were next stretched to a predetermined length by applying an axial stretching force to the individual tubing sections and heating them. Each tubing section was placed in an automated prestretching device possessing two gripping mechanisms capable of concurrent vertical motion. The prestretching device lowered the tubing section into a deionized water bath 24 heated to 90° C. (±2° C.). One of the two gripping mechanisms remained stationary while the other moved horizontally at a rate of 25%/sec. for 5 seconds. The resulting axial elongation, due to the 2.25 stretch ratio, was approximately 125%.

After the prestretch was complete, the tubing section was manually removed from the pre-stretching device and cooled for a few seconds in a deionized water bath maintained at room temperature. The tubing section was held in order to apply sufficient tension to ensure that the tube 12 did not recover from the stretch. The stretched tubing section was then removed from the water bath.

After cooling, the stretched tubing section was expanded radially using internal pressure. One end of the stretched tube was cut to provide an opening to the lumen of the tubing. In order to form a 3.75 mm balloon with a 20 mm body length, a mold having dimensions that allowed the stretched tube to blow out to the appropriate body size and balloon waist inner diameters was used.

After the tubing section was securely inside the mold, the mold was placed in a holder. The tubing section extended out the top of the mold and was fed into a Touhy clamp through which nitrogen gas was applied to the inner lumen of the tubing at 260 psi. No tension was applied to the tubing. The tubing section at the bottom of the mold was clamped off such that the pressure was maintained inside the tubing section. The mold was then gradually dipped, at a rate of 4 mm/sec., into a deionized hot water bath maintained at 95° C. (±1° C.) to a point just above the proximal waist portion of the mold. The entire dipping process consumed 15 sec. and the mold was held stationary in the bath 70 for 40 sec. Then the mold was removed from the hot water bath and cooled for approximately 10 sec. in a deionized water bath maintained at about 11° C. The balloon axially expanded during the molding by an additional 50% of its original tubing length, resulting in a total axial elongation of 175%.

Thirty balloons prepared in this manner from a single lot of tubing were used as controls.

Balloons of the invention were made in the same manner from the same lot of tubing as the controls except that the prior to the prestretching step, the tubing sections were dried in a vacuum desiccator. Five marked and preweighed tubes were used to monitor weight loss after 24 and 48 hour desiccation intervals. After 24 hours the balloons had lost an average of 0.38% of their undesiccated weight. After 48 hours the average weight loss was 0.44%.

Meanwhile, in the same desiccator, 80 unmarked tubes were dried. After 24 hours 30 tubes were removed and processed into balloons in the manner of the controls. An additional 30 balloons were made from tubes which were kept in the desiccator for 48 hours.

All balloons were inspected for "bubble" defects and observed defects were categorized as small (<0.004 inch dia.), medium (0.004–0.01 inch) and large (>0.01 inch). "Bubble" defects are typically tear shaped or American football shaped visible distortions which are sometimes, but not always, hollow. Results were as follows:

Controls: 18 "bubbles". 1 Large, 7 medium, 10 small. Four balloons had more than one "bubble".

24 hours: 11 "bubbles". 0 Large, 1 medium, 10 small. No balloons with more than one "bubble".

48 hours: 7 "bubbles". 0 Large, 3 medium, 4 small. No balloons with more than one "bubble".

Six balloons from each batch which displayed no defects were then subjected to standard burst tests by measuring the double wall thickness of the deflated balloon, inflating the balloon at incrementally increasing pressures and measuring the outside diameter at each increment until the balloon burst. Typical and average results for each batch are given in Table 1 where Dnom is diameter at nominal inflation (118 psi), Pburst and Dburst are, respectively, average burst diameter and average burst pressure.

TABLE 1

| Single wall thickness Pressure (psi) | 0 Hours 0.00062" | 24 Hours 0.00067" | 48 Hours 0.00068" |
|---|---|---|---|
| | Measured body diameter (mm) | | |
| 40 | 3.65 | 3.66 | 3.66 |
| 88 | 3.75 | 3.75 | 3.75 |
| Dnom 118 | 3.79 | 3.78 | 3.78 |
| 132 | 3.80 | 3.79 | 3.79 |
| 147 | 3.82 | 3.80 | 3.80 |
| 180 | 3.84 | 3.83 | 3.82 |
| 206 | 3.86 | 3.84 | 3.84 |
| 235 | 3.89 | 3.86 | 3.86 |
| 260 | 3.92 | 3.88 | 3.87 |
| 270 | 3.95 | 3.90 | 3.88 |
| 280 | 3.98 | 3.92 | 3.90 |
| 290 | 4.01 | 3.93 | 3.92 |
| 300 | 4.05 | 3.95 | 3.93 |
| 310 | 4.10 | 3.98 | 3.96 |
| 320 | 4.14 | 4.00 | 3.99 |
| 330 | 4.21 | 4.04 | 4.02 |
| 340 | | 4.07 | 4.05 |
| 350 | | 4.10 | 4.10 |
| 360 | | 4.11 | 4.13 |
| 370 | | | 4.18 |
| Average Results | | | |
| Pburst | 323 | 352 | 353 |
| Dburst | 4.13 | 4.11 | 4.09 |
| Distention dnom-280 | 5.0% | 3.7% | 3.2% |

EXAMPLE 2

Post Extrusion Drying

The procedures of example 1 were repeated. Average weight loss on desiccation for 24 hours was 0.34% and for 48 hours was 0.52%. Results of defect inspections were as follows:

Controls: 12 "bubbles". 3 Large, 5 medium, 4 small. Three balloons had more than one "bubble".

24 hours: 9 "bubbles". 0 Large, 4 medium, 5 small. No balloons with more than one "bubble".

48 hours: 5 "bubbles". 0 Large, 3 medium, 2 small. No balloons with more than one "bubble".

Typical and average results of burst testing are shown in Table 2:

TABLE 2

| Single wall thickness Pressure (psi) | 0 Hours 0.00062" | 24 Hours 0.00067" | 48 Hours 0.00068" |
|---|---|---|---|
| | Measured body diameter (mm) | | |
| 40 | 3.65 | 3.67 | 3,65 |
| 88 | 3.76 | 3.75 | 3.76 |
| Dnom 118 | 3.79 | 3.78 | 3.79 |
| 132 | 3.81 | 3.79 | 3.80 |
| 147 | 3.82 | 3.80 | 3.81 |
| 180 | 3.85 | 3.82 | 3.83 |
| 206 | 3.87 | 3.84 | 3.85 |
| 235 | 3.90 | 3.86 | 3.87 |
| 260 | 3.94 | 3.88 | 3.89 |
| 270 | 3.97 | 3.90 | 3.91 |
| 280 | 4.01 | 3.91 | 3.92 |
| 290 | 4.04 | 3.93 | 3.94 |

TABLE 2-continued

| Single wall thickness Pressure (psi) | 0 Hours 0.00062" | 24 Hours 0.00067" | 48 Hours 0.00068" |
|---|---|---|---|
| | Measured body diameter (mm) | | |
| 300 | 4.08 | 3.95 | 3.96 |
| 310 | 4.13 | 3.98 | 3.98 |
| 320 | 4.15 | 4.01 | 4.01 |
| 330 | | 4.05 | 4.04 |
| 340 | | 4.09 | 4.07 |
| 350 | | 4.13 | 4.10 |
| 360 | | | 4.12 |
| Average Results | | | |
| Pburst | 318 | 349 | 350 |
| Dburst | 4.13 | 4.12 | 4.12 |
| Distention dnom-280 | 5.6% | 3.4% | 3.5% |

EXAMPLE 3

Post Extrusion Drying

Four lots of balloons (25 in each lot) were stretched and blown from extruded PET tubing at a mold pressure of 180 psi. The molds were for 4.0 mm balloons. Mold dimensions were: length 100 mm; proximal ID 0.421"; distal ID 0.0315"; body ID 0.1600". The tubing lots were subjected to the following conditions before stretching and blowing:

A Tubing allowed to equilibrate in a dry room to a moisture content of 0.3%. The stretch ratio before blowing was 2.15.

B Tubing vacuum dried to moisture content of 0.05% in a desiccator prior to stretching. The stretch ratio prior to blowing was 2.15.

C Tubing allowed to equilibrate in a dry room to a moisture content of 0.3%. The stretch ratio before blowing was 2.25.

D Tubing vacuum dried to moisture content of 0.05% in a desiccator prior to stretching. The stretch ratio prior to blowing was 2.25.

In blowing each lot of stretched tubing a tension was selected to assure an axial lengthening (growth) of 17-22 mm during the blowing stage and to keep the double body wall thickness between 0.00095" and 0.00125". All balloons were inspected for "bubbles" and foreign materials. Ten of the best balloons from each lot were burst tested and distal and proximal waists were measured on one balloon from each lot. Blowing conditions and test results are shown in Table 3.

TABLE 3

| | A Comparative | B Invention | C Comparative | D Invention |
|---|---|---|---|---|
| Pressure (psi) | 180 | 180 | 180 | 180 |
| Tension | 133 | 161 | 137 | 152 |
| Average growth (mm) | 19.7 | 18.9 | 19.2 | 17.5 |
| Body double wall thickness (in) | 0.00110 | 0.00116 | 0.00108 | 0.00116 |
| Small "bubbles" (<0.010 mm) | 3 | 0 | 2 | 0 |
| Medium "bubbles" (0.004–0.10 mm) | 1 | 0 | 0 | 0 |
| Large "bubbles" (>0.010 mm) | 0 | 0 | 2 | 0 |
| Burst diameter (mm) | 4.3 | 4.3 | 4.3 | 4.3 |

TABLE 3-continued

| | A Comparative | B Invention | C Comparative | D Invention |
|---|---|---|---|---|
| Burst pressure (psi) | 328 | 336 | 327 | 337 |
| Distal wall thickness | 0.0037 | 0.0037 | 0.0034 | 0.0041 |
| Proximal wall thickness | 0.0023 | 0.0027 | 0.0028 | 0.0026 |

EXAMPLE 4

Programmed Dip Cycle

Balloons were made in a manner similar to Examples 1 and 2 except that a programmed dip cycle was used and the device of FIG. 6 was modified by replacing the pulley 66 and weight 68 with a metal cylinder containing a pressure driven piston. String 65 was attached to the piston rod so that tension could be varied by changing the pressure in the cylinder so as to move the cylinder up or down. The program was as follows, where pressures applied to the cylinder have been converted to equivalent tensions applied to the tubing.

| Mold specification: | Proximal waist ID | 0.0352 inches |
|---|---|---|
| | Body ID | 0.1195 inches |
| | Distal waist ID | 0.0280 inches |
| | Cone angle | 15° |
| Prestretch stretch ratio: | | 2.25 |
| Program: | bath at | 95 °C. |
| (1) | pressure to | 295 psi |
| | tension to | 60 g |
| | hold at A | 5 seconds |
| | dip to D | 5 seconds |
| | hold at D | 5 seconds |
| (2) | pressure to | 120 psi |
| | tension to | 60 g |
| | dip to F | 10 sec |
| | hold at F | 5 seconds |
| (3) | pressure to | 295 psi |
| | tension to | 200 g |
| | dip to G | 1 sec |
| | hold at G | 1 sec |
| | dip to H | 10 sec |
| | hold at H | 25 seconds |

Average wall thickness of the balloons produced in this way were: body single wall, 0.00045 inches; proximal wall, 0.00141 inches; distal wall, 0.00169 inches.

In the remaining examples the modified version of the device of FIG. 6 which is described in the previous example was employed and a simplified programmed dipping and blowing cycle was used. In this program the mold was dipped from the initial position, A in FIG. 4, to a first depth approximately at the midpoint of the first cone i.e. midway between C and D, held and then after reducing the pressure, dipped to a second depth approximately at the midpoint of the second cone, i.e. between E and F, held and then after increasing pressure and tension, dipped to the final position H, slowing down near the final position, and then holding for a third interval before being removed and dipped in the cooling bath.

EXAMPLE 5

Programmed Dip Cycle 2.5 mm balloons were made from 0.0125"×0.0272" PET extruded tubes. The extruded tubes were stretched 2.25 times of the original length at 90° C. The stretched tubes were then blown into balloons at 95° C. The mold pressure was 250 psi at proximal end, 130 psi at body, 290 psi at distal end. The pulling tension was 25 grams at proximal end and body, 180 grams at distal end. The dip cycle was 5 seconds hold at initial position, 5 sec. dip to first depth, 5 sec hold at first depth; 10 seconds dip to second position, 8 seconds hold at second position; 6 seconds to dip to the final position, holding for 30 seconds before removing and quenching in a cooling bath. The balloon has a body wall (single wall) of 0.00039", proximal waist wall of 0.0010", distal waist wall of 0.0012", pressure burst at 343 psi. The compliance at 118–279 psi is less than 7%. The result is shown in Table 4.

EXAMPLE 6

Programmed Dip Cycle 3.0 mm balloons were made from 0.0149×0.0311 PET tube. Stretching and blowing temperatures were the same as example 1. The mold pressure was 280 psi at proximal end, 130 psi at body, 290 psi at distal end. The pulling tension was 50 grams at proximal end and 35 grams at body, 250 grams at distal end. The dip cycle was as in Example 5. The balloon has a body wall of 0.00040", proximal waist wall of 0.0010", distal waist wall of 0.0011", pressure burst at 320 psi. The compliance at 118–279 psi was less than 7%. The result is shown in Table 4.

EXAMPLE 7

Programmed Dip Cycle 4.0 mm balloons were made from 0.0195×0.0395" PET tube. Stretching and blowing temperatures were the same as example 1. The mold pressure was 280 psi at proximal end, 130 psi at body, 290 psi at distal end. The pulling tension was 90 grams at proximal end and 90 grams at body, 350 grams at distal end. The dip cycle was as in Example 5. The balloon has a body wall of 0.00046", proximal waist wall of 0.0022", distal waist wall of 0.0023", pressure burst at 295 psi. The compliance at 118–279 psi was less than 7%. The result is shown in Table 4.

TABLE 4

| | Comparative Balloon* | Invention Balloon | % Reduction |
|---|---|---|---|
| Size: 2.5 mm | | | |
| Balloon wall/inch | .00056" | .00039" | 30 |
| Distal waist wall | .0031" | .0012" | 61 |
| Prox. waist wall | .0028" | .0010" | 64 |
| Profile reduced** | | .0038" | |
| Size: 3.0 mm | | | |
| Balloon wall/inch | .00056" | .00040" | 29 |
| Distal waist wall/inch | .0041" | .0010" | 76 |
| Prox. waist wall/inch | .0035" | .0011" | 69 |
| Profile reduced | | .0062" | |
| Size: 4.0 mm | | | |
| Balloon wall/inch | .00062 | .00046" | 26 |
| Distal waist wall/inch | .0051" | .0023 | 55 |
| Prox. waist wall/inch | .0049" | .0022" | 55 |
| Profile reduced | | .0056" | |

*Comparative balloons were commercial balloons of comparable body diameter and body wall thickness employed on NC-Shadow ™ catheters sold by SciMed Life Systems Inc., Maple Grove MN, USA and prepared by a process using constant pressure and tension.
**Profile reduced is calculated from distal waist wall thicknesses of the comparative balloons.

EXAMPLE 8

Balloons as prepared in example 6 were mounted on catheters of comparable configuration to the NC-Shadow™ catheter of the same balloon body dimension and the resulting catheters were compared for recrossing force, pulling force, trackability and surface friendship. Recrossing force is the force to push a deflated balloon through a 0.049 inch lesion after the balloon has been inflated to 12 atm. for 1 min. Pulling force is the force to pull a deflated balloon catheter back through a 7F guide catheter after balloons were inflated to 12 atm for 1 min. All of the measurements were done at 37° C. Results are provided in table 5.

TABLE 5

| | Comparative catheter | Invention catheter | % Reduction |
|---|---|---|---|
| Recrossing Force (lb) | 0.29 | 0.16 | 45 |
| Pulling force from guide (lb) | 0.13 | 0.10 | 23 |
| Trackability | | greatly improved | |
| Surface friendship | rough | good | |

EXAMPLE 9

Programmed Dip Cycle 3.0 mm balloons were made from 0.0149×0.0307" PET tube. The tubes were dried up to 100 ppm moisture (in the range of 10–200 ppm) before stretching and blowing. The tube was stretched 2.15 times of the original length at 90° C. The stretched tube was then blown into balloon at 95° C. The mold pressure was 270 psi at proximal end, 110 psi at body, 270 psi at distal end. The pulling tension was 22 grams at proximal end and body, 50 grams at distal end. The dip cycle was as in Example 5. The balloon has a body wall of 0.00040", proximal waist wall of 0.0013", distal waist wall of 0.0013", pressure burst at 330 psi. The compliance at 118–279 psi was less than 7%.

EXAMPLE 10

Programmed Dip Cycle 3.0 mm polyethylene copolymer balloons were made from tubing having an OD of 0.032" and an ID of 0.0215". The tubes were not stretched before blowing. The tubes were treated with E-beams to crosslink the polymer material. The blowing temperature was 90° C. Mold pressure was 120 psi at both ends, 80 psi at body. Pulling tension was 500 grams at the second end, 0 grams at body. Balloon wall thickness of 0.0250"–0.0275" and burst pressure of 188 psi were the same as those with fixed pressure and without tension. However, the waist walls of the second ends of the resulting balloons were reduced 10–30%.

Although the present invention has been described with reference to preferred embodiments, workers skilled in the art will recognize that changes may be made in form and detail without departing from the spirit and scope of the invention.

What is claimed is:

1. In a method of preparing an oriented balloon of thermoplastic material comprising extruding a hollow tube of the thermoplastic material, and subsequently expanding the tube by subjecting the tubing, while in a mold, to an elevated temperature and an increased interior pressure to produce an oriented balloon, the improvement wherein the tube is subjected to a drying step, prior to said expanding step, thereby increasing the strength of the balloon relative to a reference balloon prepared in the same manner, except for said drying step.

2. A method as in claim 1 wherein the extruded tube is subjected to a stretching step before said expanding step and the tube is dried before said stretching step.

3. A method of preparing an oriented balloon as in claim 1 wherein the thermoplastic material is a polyethylene terephthalate homopolymer or copolymer.

4. A method of forming a balloon for a catheter, the balloon having a first waist portion, a body portion and a second waist portion, the method comprising placing tubing of a thermoplastic material in a mold and blowing the balloon by pressurizing and tensioning the tubing while gradually dipping the mold into a heated heat transfer media so as to sequentially blow the first waist, the body and the second waist portions of the balloon, the tubing being subjected to a relatively lower pressure while the body portion is blown than while the first and second waist portions are blown.

5. A method as in claim 5 wherein the tubing is also subjected to a relatively a lower tension while the body portion is blown than while the first and second waist portions are blown.

6. In a process for forming an elongated balloon having a longitudinal body portion, first and second waist portions of reduced diameter relative to the body portion at opposite ends of the balloon and first and second cone portions connecting corresponding waist portions and respective ends of the longitudinal body portion, the process comprising the steps of placing an extruded and stretched tubular preform in a mold having an internal form corresponding to the desired outer configuration of the balloon, and forming the balloon by applying axial tension and internal pressure to the preform upon dipping of the mold into a heated heat transfer media, the improvement comprising that the forming step comprises:

pressurizing the preform to a first pressure in the range of 150–320 psi and applying a first tension in the range of 5–150 g;

dipping the mold to a first depth in the range of from the transition (C) from the first waist to the first cone to the transition (D) from the first cone to the body portion of the balloon while maintaining the first tension and the first pressure, and thereby expanding at least one portion of the preform in the mold;

pressurizing the preform to a second pressure less than the first pressure and between 80 and 170 psi and setting a second tension in the range of the first tension;

dipping the mold to a second depth in the range of from the transition (E) from the body portion to the second cone portion to the transition (F) from the second cone to the second waist while maintaining the second tension and the second pressure;

pressurizing the preform to a third pressure higher than the second pressure and between 150 and 320 psi and applying to the preform a third tension, higher than the first tension, and then, dipping the mold to a third depth (H) beyond the depth of the second waist while maintaining the third tension and the third pressure.

7. A method as in claim 6 wherein the third tension is in the range of 50 to 700 g.

8. In a process for forming an elongated balloon having a longitudinal body portion, first and second waist portions of reduced diameter relative to the body portion at opposite ends of the balloon and first and second cone portions connecting corresponding waist portions and respective ends of the longitudinal body portion, the process comprising the steps of placing an extruded and stretched tubular preform in a mold having an internal form corresponding to the desired outer configuration of the balloon, and forming the balloon by applying axial tension and internal pressure to the preform upon dipping of the mold into a heated heat transfer media, the improvement comprising that the forming step comprises:

pressurizing the preform to a first pressure in the range of 150–320 psi and applying a first tension in the range of 5–150 g;

dipping the mold to a first depth in the range of from the transition (C) from the first waist to the first cone to the transition (D) from the first cone to the body portion of the balloon while maintaining the first tension and the first pressure, and thereby expanding at least one portion of the preform in the mold;

holding the mold at the first depth for a predetermined first time interval while maintaining the first tension and the first pressure;

pressurizing the preform to a second pressure less than the first pressure and between 80 and 170 psi and setting a second tension in the range of the first tension;

dipping the mold to a second depth in the range of from the transition (E) from the body portion to the second cone portion to the transition (F) from the second cone to the second waist while maintaining the second tension and the second pressure;

holding the mold at the second depth while maintaining the second tension and the second pressure for a predetermined second time interval;

pressurizing the preform to a third pressure higher than the second pressure and between 150 and 320 psi and applying to the preform a third tension, higher than the first tension;

dipping the mold to a third depth (H) beyond the depth of the second waist while maintaining the third tension and the third pressure, and then holding the mold at the third depth for a predetermined third time interval while maintaining the third tension and third pressure.

9. The method as in claim 8 wherein said first time interval is between 1 and 40 seconds, the second time interval is between 1 and 40 seconds and the third time interval is between 10 and 100 seconds.

10. The method of claim 8 wherein the difference between said second and third pressures is at least 100 psi.

11. The method of claim 8 wherein the thermoplastic material is a polyethylene terephthalate homopolymer or copolymer.

12. The method of claim 11 wherein said heat transfer media is heated to a temperature of 90° C. to 100° C.

13. The method of claim 6 wherein the extruded tubular preform is dried after being extruded and prior to being stretched.

14. The method of claim 13 wherein the extruded tubular preform is dried to a moisture content of less than 0.15 weight %.

15. The method of claim 6 wherein the second tension is the same as the first tension.

16. The method of claim 6 wherein the second tension is less than the first tension.

* * * * *

UNITED STATES PATENT AND TRADEMARK OFFICE
CERTIFICATE OF CORRECTION

PATENT NO. : 5,714,110
DATED : Feb. 3, 1998
INVENTOR(S) : LIXIAO WANG ET AL

It is certified that error appears in the above-identified patent and that said Letters Patent is hereby corrected as shown below:

Col. 1, line 27, delete "tureen" and insert -- lumen--;

Col. 1, line 67, delete "32,993" and insert -- 32,983 --;

Col. 2, line 1, delete "5,108,412" and insert -- 5,108,415 --;

Col. 5, line 21, before "dried" insert -- suitably --;

Col. 5, line 53, delete "mount" and insert -- amount --;

Col. 7, line 1, delete "I" before "The";

Signed and Sealed this

Eighth Day of September, 1998

Attest:

BRUCE LEHMAN

*Attesting Officer*     *Commissioner of Patents and Trademarks*